United States Patent
Shinkawa et al.

(10) Patent No.: US 9,212,368 B2
(45) Date of Patent: Dec. 15, 2015

(54) ASPERGILLUS MUTANT STRAIN

(71) Applicant: HONDA MOTOR CO., LTD., Tokyo (JP)

(72) Inventors: Satoru Shinkawa, Wako (JP); Shigenobu Mitsuzawa, Wako (JP); Maiko Tanaka, Wako (JP)

(73) Assignee: HONDA MOTOR CO., LTD., Tokyo (JP)

(*) Notice: Subject to any disclaimer, the term of this patent is extended or adjusted under 35 U.S.C. 154(b) by 0 days.

(21) Appl. No.: 14/600,103

(22) Filed: Jan. 20, 2015

(65) Prior Publication Data

US 2015/0203855 A1    Jul. 23, 2015

(30) Foreign Application Priority Data

Jan. 22, 2014 (JP) .................................. 2014-009748

(51) Int. Cl.
*C12N 9/62* (2006.01)
*C12N 9/20* (2006.01)
*C12N 15/80* (2006.01)
*C12N 9/42* (2006.01)
*C12N 9/24* (2006.01)

(52) U.S. Cl.
CPC ............... *C12N 15/80* (2013.01); *C12N 9/2437* (2013.01); *C12N 9/2445* (2013.01); *C12N 9/2482* (2013.01)

(58) Field of Classification Search
CPC ............. C12N 9/20; C12N 9/62; C12N 15/80
USPC ........................................................ 435/252.3
See application file for complete search history.

(56) References Cited

PUBLICATIONS

Maruyama et al., Biotechnol. Lett., 2008, 30, 1811-1817.*
Contribution Ratios of amyA, amyB, amyC Genes to High-Level a-Amylase Expression in Aspergillus oryzae, Takashi Nemoto, Bioscience, Biotechnology, and Biochemistry, 2012, vol. 76(8), pp. 1477-1483, Discussed in specification, English Text.
Transformation System for Aspergillus oryzae with Double Auxotrophic Mutations, niaD and sC, Osamu Yamada et al., Bioscience, Biotechnology, and Biochemistry, 1997, vol. 61(8), pp. 1367-1369, Discussed in specification, English text.
Development of an efficient gene-targeting system in Aspergillus luchuensis by deletion of the non-homologous end joining system, Journal of Bioscience and Bioengineering, 2011, vol. 112(6), pp. 529-534, Discussed in specification, English text.
A defect of LigD (human Lig4 homolog) for nonhomologous end joining significantly improves efficiency of gene-targeting in Aspergillus oryzae, Osamu Mizutani et al., Fungal Genetics and Biology, 2008, vol. 45, pp. 878-889, Discussed in specification, English text.
The development of a homologous transformation system for Aspergillus oryzae based on the nitrate assimilation pathway: A convenient and general selection system for filamentous fungal transformation, Shiela E. Unkles et al., Mol. Gen. Genet., vol. 218, pp. 99-104 (1989), Discussed in specification, English text.

* cited by examiner

*Primary Examiner* — Maryam Monshipouri
(74) *Attorney, Agent, or Firm* — Rankin, Hill & Clark LLP

(57) ABSTRACT

An *Aspergillus* mutant strain obtained by deleting a ligD gene from an auxotrophic mutant strain of *Aspergillus oryzae* strain AOK27L.

10 Claims, 4 Drawing Sheets

ASPERGILLUS MUTANT STRAIN

TECHNICAL FIELD

The present invention relates to an *Aspergillus* mutant strain which is suitable for solid culture and is also suitable as a host for genetic recombination, a transformant obtained from the *Aspergillus* mutant strain, and a method of producing a saccharifying enzyme using the transformant.

Priority is claimed on Japanese Patent Application No. 2014-009748, filed Jan. 22, 2014, the content of which is incorporated herein by reference.

BACKGROUND ART

In addition to environmental problems such as global warming and air pollution, from concerns related to the energy supply for transport such as the significant increase in crude oil prices and crude oil depletion expected in the near future (peak oil), in recent years, development of alternative energy to petroleum is a very important issue. Cellulose-based biomass, such as plant biomass and lignocellulose, which is the most abundant renewable energy source on the earth, is expected as an alternative resource to petroleum.

By culturing an *Aspergillus* fungus (koji mold) producing a saccharifying enzyme on the surface of the solid biomass such as rice straw and corn stover, it is possible to subject the biomass to a saccharification treatment. By using a transformant obtained by introducing a gene for a saccharifying enzyme with higher saccharification capability into an *Aspergillus* strain, it is possible to improve the efficiency of the saccharification treatment.

On the other hand, when introducing a foreign gene into a microorganism such as an *Aspergillus* strain for transformation, in order to selectively pick only microorganisms into which the foreign gene of interest has been introduced, a method of using an auxotrophic strain as a host which is deficient of the pyrG gene (orotidine-5'-phosphate decarboxylase), sC gene, niaD gene and the like has been generally used (see, for example, Non-Patent Document 1 or 2). For example, when using a strain that became auxotrophic for uridine due to deletion of the pyrG gene as a host strain and culturing in a uridine-free medium after introducing thereinto a combination of the gene of interest and the pyrG gene, since only transformants are able to grow, it is possible to efficiently select genetically modified fungi.

In addition, a method has been known to date for improving the homologous recombination efficiency due to deletion of the ligD gene (encoding a DNA ligase) (for example, see Non-Patent Document 3) and also for recycling the pyrG gene by utilizing homologous recombination (marker recycling) (for example, see Non-Patent Document 4). When carrying out gene recombination, by deleting the ligD gene, it is possible to suppress random introduction of the target gene into the genome and to efficiently construct a strain in which the gene is introduced into a targeted site. In addition, through the marker recycling method, it is possible to use one marker gene for the selection in multiple gene transfers, although only the selection for a single gene transfer has been carried out conventionally for one marker gene.

PRIOR ART DOCUMENTS

Non-Patent Documents

[Non-Patent Document 1] Nemoto, et. al., Bioscience, Biotechnology, and Biochemistry, 2012, vol. 76 (8), p. 1477-1483.

[Non-Patent Document 2] Yamada, et. al., Bioscience, Biotechnology, and Biochemistry, 1997, vol. 61 (8), p. 1367-1369.

[Non-Patent Document 3] Takahashi, et. al., Journal of Bioscience and Bioengineering, 2011, vol. 112 (6), p. 529-534.

[Non-Patent Document 4] Mizutani, et. al., Fungal Genetics and Biology, 2008, vol. 45, p. 878-889.

SUMMARY OF THE INVENTION

Problems to be Solved by the Invention

The present invention has an object of providing an *Aspergillus* mutant strain which exhibits high enzyme productivity by solid culture using herbaceous biomass, which is auxotrophic, and in which a structural gene can be introduced into the targeted site; a transformant obtained from the *Aspergillus* mutant strain; and a method of producing a saccharifying enzyme using the transformant.

Means for Solving the Problems

An *Aspergillus* mutant strain, a transformant and a method of producing a saccharifying enzyme according to the present invention include the following aspects [1] to [10].

[1] An *Aspergillus* mutant strain obtained by deleting a ligD gene from an auxotrophic mutant strain of *Aspergillus oryzae* strain AOK27L.

[2] The *Aspergillus* mutant strain according to the aforementioned aspect [1], wherein the aforementioned auxotrophic mutant strain is a uridine auxotrophic mutant strain of *Aspergillus oryzae* strain AOK27L in which a pyrG gene is completely or partially deleted.

[3] The *Aspergillus* mutant strain according to the aforementioned aspect [2], wherein the aforementioned uridine auxotrophic mutant strain is an *Aspergillus oryzae* strain H01 (accession number: NITE BP-01749).

[4] The *Aspergillus* mutant strain according to the aforementioned aspect [1] which is an *Aspergillus oryzae* strain H02 (accession number: NITE BP-01750).

[5] A transformant obtained by introducing a pyrG gene and a saccharifying enzyme gene into the *Aspergillus* mutant strain described in any one of the aforementioned aspects [2] to [4].

[6] The transformant according to the aforementioned aspect [5], wherein the aforementioned saccharifying enzyme gene is at least one gene selected from the group consisting of a cellobiohydrolase gene, a β-glucosidase gene, an endoxylanase gene, an arabinofuranosidase gene, a glucuronidase gene and an endoglucanase gene.

[7] The transformant according to the aforementioned aspect [5], wherein the aforementioned saccharifying enzyme gene is at least one gene selected from the group consisting of a cellobiohydrolase gene derived from *Acremonium cellulolyticus*, a β-glucosidase gene derived from *Acremonium cellulolyticus*, an endoxylanase gene derived from a fungus belonging to the genus *Thermoascus*, an arabinofuranosidase gene derived from *Acremonium cellulolyticus* and a glucuronidase gene derived from *Acremonium cellulolyticus*.

[8] The transformant according to any one of the aforementioned aspects [5] to [7], wherein the pyrG gene and the aforementioned saccharifying enzyme gene are incorporated into a chromosome.

[9] A method of producing a saccharifying enzyme, the method including culturing the transformant described in any one of the aforementioned aspects [5] to [8] on a solid medium which is used herbaceous biomass as a substrate.

[10] The method of producing a saccharifying enzyme according to the aforementioned aspect [9], wherein the aforementioned herbaceous biomass is rice straw or corn stover.

Effects of the Invention

Since the *Aspergillus* mutant strain according to the present invention is suitable for solid culture and is also an auxotrophic strain, it is suitable as a host for genetic recombination for introducing a foreign gene. In addition, since the non-homologous recombination is suppressed due to deletion of the ligD gene, it is possible to introduce a structural gene to the targeted site in the chromosome. For this reason, a transformant obtained by introducing a saccharifying enzyme gene into the *Aspergillus* mutant strain is capable of producing a saccharifying enzyme efficiently by solid culture.

BEST MODE FOR CARRYING OUT THE INVENTION

<*Aspergillus* Mutant Strain>

Figure 1:
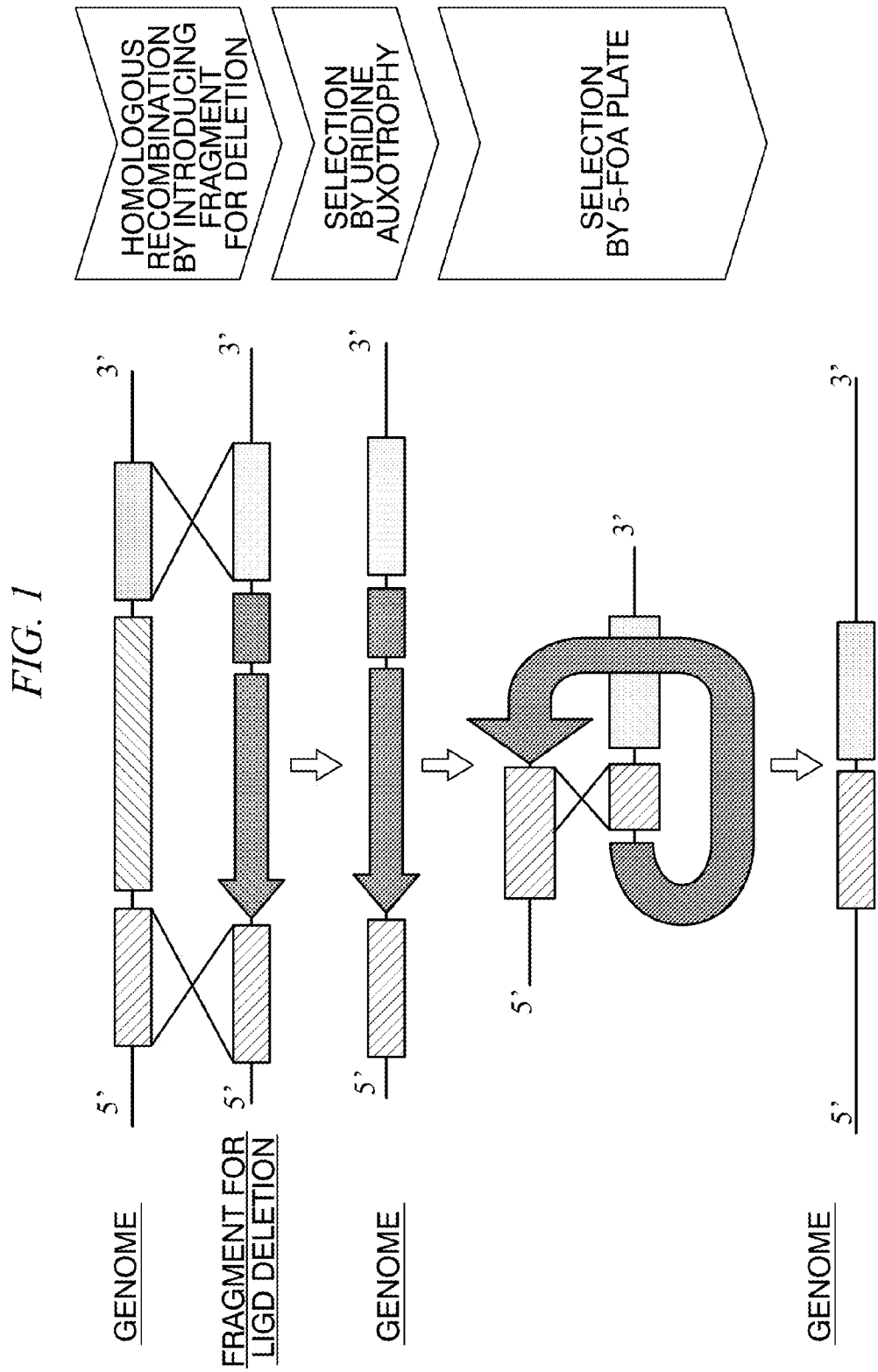
FIG. 1 is a schematic diagram of a method of producing an *Aspergillus* mutant obtained by deleting the ligD gene from a mutant strain auxotrophic for uridine by using a marker recycling method.
Figure 2:
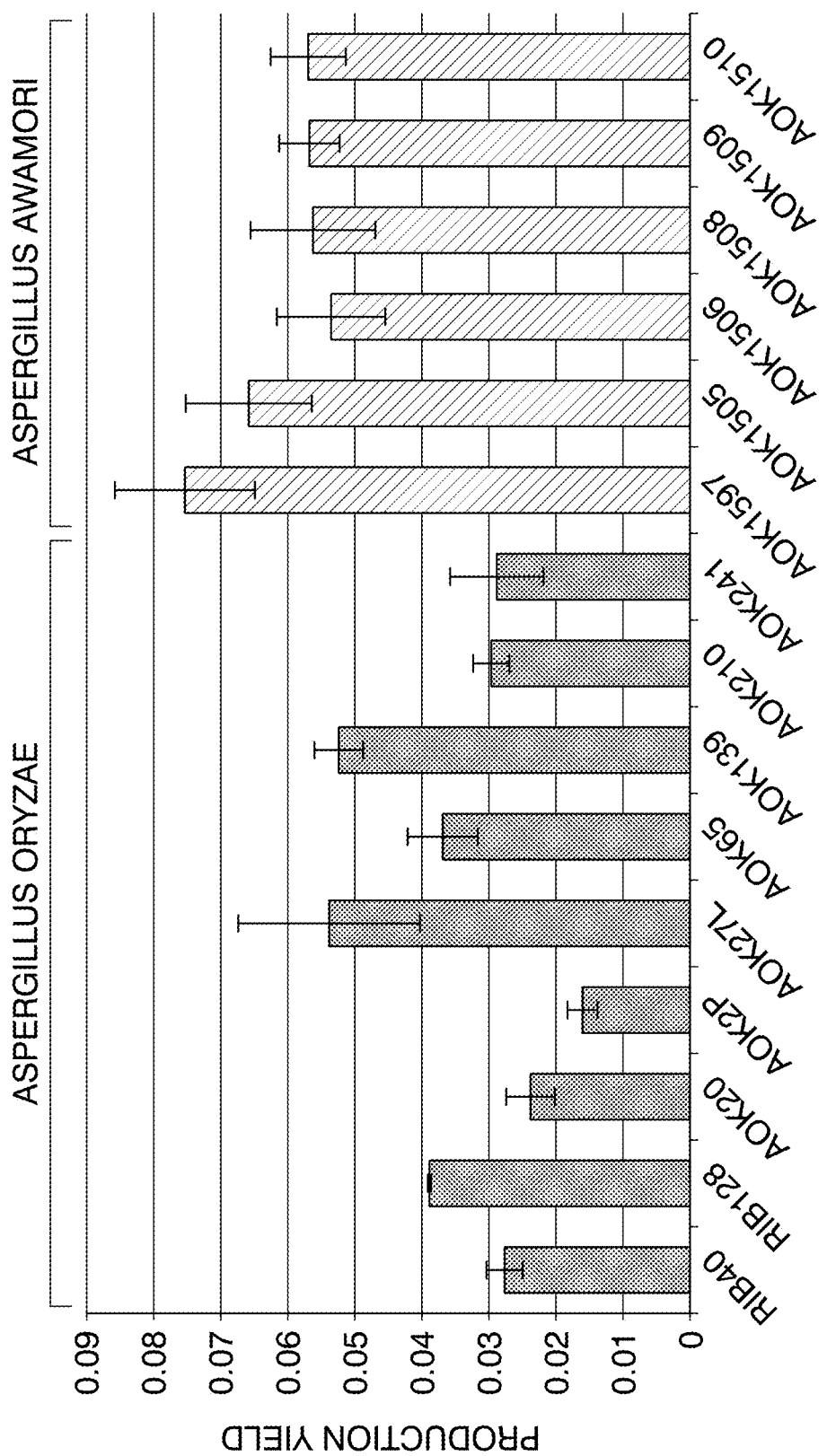
FIG. 2 is a diagram showing the measurement results of the enzyme production yield of the strains belonging to *Aspergillus oryzae* or *Aspergillus awamori* in Reference Example 1.

An *Aspergillus* mutant strain according to the present invention is characterized by deleting a ligD gene from an auxotrophic mutant strain of the *Aspergillus oryzae* strain AOK27L (available from Akita Konno Co., Ltd.) (hereinafter, abbreviated as the "AOK27L strain" in some cases) which is obtained by deleting the function of a specific gene involved in the synthesis of a aspecific nutrient and the like to acquire auxotrophy. The ligD gene is a gene encoding an enzyme required for repairing the random nicks that occur in the genome. Since the ligD gene is deleted in the *Aspergillus* mutant strain according to the present invention, non-homologous recombination does not take place, and the introduction of genes at random positions in the chromosome can be prevented. Therefore, it is possible to introduce a foreign gene to the targeted site in the chromosome by homologous recombination.

In the present invention, the term simply "auxotrophic" means the property which requires a specific nutrient.

In addition, the *Aspergillus* mutant strain according to the present invention exhibits auxotrophy. For this reason, by using the *Aspergillus* mutant strain according to the present invention as a host for genetic recombination, it is possible to obtain a genetically modified strain efficiently. As the auxotrophy exhibited by the mutant strain of *Aspergillus* according to the present invention, auxotrophy for uridine is preferred.

The *Aspergillus* mutant strain according to the present invention can be cultured by the same culture medium and culture conditions as those for the AOK27L strain with the exception that the culture medium is added with a required nutrient (medium supplemented with uridine in the case of uridine auxotrophy).

(Auxotrophic Mutant Strain)

An auxotrophic mutant strain serving as a parent strain for the *Aspergillus* mutant strain according to the present invention is a strain which is obtained by completely or partially deleting a gene involved in the synthesis of a specific nutrient or the like of the AOK27L strain, and is therefore provided with auxotrophy. As shown in Reference Example 1 to be described later, the AOK27L strain is superior to other strains of *Aspergillus oryzae* in terms of the enzyme production efficiency when cultured on a solid medium. In other words, the *Aspergillus* mutant strain according to the present invention is a strain obtained by conferring auxotrophy to a strain originally exhibiting a high enzyme production efficiency in solid culture, and further deleting the ligD gene.

For example, in order to confer auxotrophy for uridine to the AOK27L strain, the pyrG gene is completely or partially deleted. In addition, the sC gene or niaD gene may be completely or partially deleted. The method for completely or partially deleting the pyrG gene and the like is not particularly limited, and can be suitably selected and used from amongst known techniques in the genetic recombination of microbes, such as a protoplast-PEG method and a natural mutagenesis method. As a parent strain for the *Aspergillus* mutant strain according to the present invention, a mutant strain auxotrophic for uridine is preferred, and the *Aspergillus oryzae* strain H01 (hereinafter, abbreviated as the "HO1 strain" in some cases) is more preferred.

The term "partially deleted" means that a deletion of a gene, such as an enzyme catalytic function is lost. As the deletion, for example, a deletion of an initiation codon of a gene, an introduction of a stop codon into the middle of a gene and the like can be mentioned.

(Method of Deleting the ligD Gene)

As a method of producing an *Aspergillus* mutant obtained by deleting the ligD gene from an auxotrophic mutant strain, such as the aforementioned mutant strain auxotrophic for uridine, a method using a marker recycling method is preferred.

FIG. 1 shows a schematic diagram of a scheme of recycling method of the pyrG gene with respect to the aforementioned uridine-requiring mutant strain. A DNA fragment (hereinafter, abbreviated as the "fragment for ligD deletion" in some cease) containing the pyrG gene sequence is used for the homologous recombination in order to delete the ligD gene. The fragment for ligD deletion is obtained by adding sequences homologous to the sequences upstream and downstream of the ligD gene in the chromosome to the upstream side (5' end side) and the downstream side (3' end side) of the pyrG gene sequence, respectively, and further adding, to the downstream of the pyrG gene sequence, a region homologous to near the region (for example, the region in which from 300 base pair to 600 base pair, from the 5' terminal of the pyrG gene sequence) of upstream side of the pyrG gene sequence. The fragment for ligD deletion introduced into the uridine-requiring mutant strain causes homologous recombination in a region where the ligD gene is present in the chromosome, and, as a result, the pyrG gene is incorporated in place of the ligD gene. By growing on a uridine-free medium, only the transformant into which the pyrG gene has been incorporated is selected. By culturing the selected clones with a 5-FOA plate medium, the pyrG gene is excised by intramolecular homologous recombination, and, as a result, an *Aspergillus* mutant strain (*Aspergillus* mutant strain according to the present invention) in which both the ligD gene and the pyrG gene are deleted can be obtained by obtaining colonies that have grown by becoming 5-FOA resistant once again.

In other words, a method of producing an *Aspergillus* mutant obtained by deleting the ligD gene from an auxotrophic mutant strain of AOK27L strain according to the present invention includes obtaining the auxotrophic mutant strain of AOK27L strain by deleting completely or partially a gene involved in the synthesis of a nutrient or the like by the genetic recombination; and deleting the ligD gene from the auxotrophic mutant strain by performing a marker recycling method.

A transformant obtained by introducing a saccharifying enzyme gene into the *Aspergillus* mutant strain according to the present invention is capable of producing the saccharifying enzyme highly efficiently. By introducing a gene deleted from the AOK27L strain in order to confer auxotrophy together with the saccharifying enzyme gene at the time of producing the transformant, a strain into which the saccharifying enzyme gene has been introduced can be obtained efficiently by using the presence and absence of auxotrophy as an indicator.

<Transformant>

The transformant according to the present invention is characterized in that the pyrG gene and the saccharifying enzyme gene have been introduced into, among the *Aspergillus* mutant strain according to the present invention, the uridine-requiring mutant strain in which the pyrG gene is completely or partially deleted. By introducing both the pyrG gene and the saccharifying enzyme gene, it becomes possible to grow the transformant even in a uridine-free medium. Therefore, by culturing the *Aspergillus* strains after gene introduction in a uridine-free medium, it is possible to select only transformants according to the present invention.

In the transformant according to the present invention, although the pyrG gene and the saccharifying enzyme gene may be maintained as extrachromosomal genes outside the chromosome, in terms of expression stability of the saccharifying enzyme, those that are integrated into the chromosome are more preferred.

For example, by introducing an expression vector incorporating an expression cassette for expressing the pyrG gene and an expression cassette for expressing the saccharifying enzyme gene into the aforementioned *Aspergillus* mutant strain, a transformant can be obtained. It should be noted that although both of an expression vector incorporating the expression cassette for expressing the pyrG gene and an expression vector incorporating the expression cassette for expressing the saccharifying enzyme gene may be introduced into the aforementioned *Aspergillus* mutant strain, in terms of the selection accuracy by uridine auxotrophy, it is more preferable to carry out a transformation process by placing the expression cassettes of both genes on a single expression vector.

In other words, a method of producing a transformant according to the present invention may include introducing an expression vector incorporating an expression cassette for expressing the pyrG gene and an expression cassette for expressing the saccharifying enzyme gene into the aforementioned *Aspergillus* mutant strain; or may include introducing both of an expression vector incorporating the expression cassette for expressing the pyrG gene and an expression vector incorporating the expression cassette for expressing the saccharifying enzyme gene m into the aforementioned *Aspergillus* mutant strain.

Here, the expression cassette refers to a combination of DNA required for expressing a structural gene (a gene which determines the primary structure of a protein, namely, the amino acid sequence) and contains the structural gene and a promoter and terminator that function inside the host cell. The expression cassette may further include either one or more of a 5'-untranslated region and 3'-untranslated region. In addition, the expression cassette for expressing the pyrG gene and the expression cassette for expressing the saccharifying enzyme gene may be separate expression cassettes, or both the pyrG gene and the saccharifying enzyme gene may be included within a single expression cassette as the structural genes.

Further, as an expression vector for incorporating the expression cassette, it is possible to use those that are selected appropriately from the known vectors that can be used for the transformation of *Aspergillus* strains, including *Aspergillus oryzae*, and that are modified appropriately if needed.

The transformation method for introducing the expression vector into the *Aspergillus* mutant strain according to the present invention is not particularly limited, and can be carried out by various methods used for introducing genes to *Aspergillus* strains, including *Aspergillus oryzae*. As the transformation method, for example, a protoplast-PEG method, a PEG-calcium method (Mol. Gen. Genet., Vol. 218, p. 99-104 (1989)), an electroporation method, an *Agrobacterium* method and the like can be mentioned. By culturing on a uridine-free medium following transformation, only the transformant into which the expression cassette has been introduced is grown and selected.

Since the ligD gene is deleted in the *Aspergillus* mutant strain according to the present invention, each expression cassette is incorporated into the chromosome by using homologous recombination. For this reason, the expression cassette is incorporated into an expression vector in a state of being sandwiched by the base sequences of the upstream side and downstream side (500 bp to 2000 bp, respectively)) of the site into which the expression cassette is intended to be introduced in the chromosome. By homologous recombination, the pyrG gene and the saccharifying enzyme gene can be introduced efficiently into the targeted site within the chromosome.

As a saccharifying enzyme gene to be introduced into the *Aspergillus* mutant strain according to the present invention, a gene encoding a saccharifying enzyme used in the saccharification of cellulose-based biomass, such as plant biomass and lignocellulose is generally preferred. As the saccharifying enzyme gene, for example, an endoglucanase of glucoside hydrolase (cellulase or endo-1,4-β-D-glucanase, EC 3.2.1.4) gene, an exo-type cellobiohydrolase (1,4-β-cellobiosidase or cellobiohydrolase, EC 3.2.1.91) gene, a β-glucosidase (EC 3.2.1.21) gene, a xylanase (endo-1,4-β-xylanase, EC 3.2.1.8) serving as a hemicellulase gene, an arabinofuranosidase (EC 3.2.1.55) gene, a glucuronidase (EC 3.2.1.31) gene and the like can be mentioned. The saccharifying enzyme gene to be introduced into the *Aspergillus* mutant strain according to the present invention may be only one type, or a combination of two or more types may be introduced.

As a saccharifying enzyme gene to be introduced into the *Aspergillus* mutant strain according to the present invention, a gene encoding a saccharifying enzyme exhibiting a strong saccharification capacity is preferred. For example, it is preferable to introduce one type or a combination of two or more types of genes selected from the group consisting of a cellobiohydrolase gene derived from *Acremonium cellulolyticus*, a β-glucosidase gene derived from *Acremonium cellulolyticus*, an endoxylanase gene derived from a fungus belonging to the genus *Thermoascus*, an arabinofuranosidase gene derived from *Acremonium cellulolyticus* and a glucuronidase gene derived from *Acremonium cellulolyticus*.

As a saccharifying enzyme gene to be introduced into the *Aspergillus* mutant strain according to the present invention, a gene encoding a saccharifying enzyme with high heat resistance (for example, a saccharifying enzyme having an activity at 80° C. or more) is also preferred. This is due to the fact that by carrying out the saccharification process for the cellulose-based biomass at a relatively high temperature (for example, 50° C. to 80° C.), the efficiency of saccharification can be further enhanced.

As the saccharifying enzyme with high heat resistance, for example, a xylanase derived from *Thermoascus aurantiacus*, a β-xylosidase derived from Thermotoga maritime and the like can be mentioned.

<Production Method of Saccharifying Enzyme>

A method of producing a saccharifying enzyme according to the present invention is characterized in that the transformant according to the present invention is cultured on a solid medium which is used herbaceous biomass as a substrate. Since the transformant according to the present invention is derived by using the AOK27L strain that originally exhibits a high enzyme production yield in solid culture as a parent strain, it can produce the saccharifying enzyme with high yield by solid culture than the transformants produced by using other *Aspergillus oryzae* strains as parent strains.

The solid used as a base in this method is preferably herbaceous biomass, and more preferably rice straw or corn stover.

The herbaceous biomass may be pretreated by a step which includes maintaining under an acidic condition such as dilute sulfuric acid or under an alkaline such as ammonia.

In other words, a method of producing a saccharifying enzyme of the present invention includes culturing the transformant according to the present invention on a solid medium which is used herbaceous biomass as a substrate. The method may further include pretreating the herbaceous biomass, and may include isolating a saccharifying enzyme by recovering and purifying the cultures.

The culturing on a solid medium, for example, includes adding the transformant according to the present invention (for example, inoculated with $1 \times 10^5$ to $1 \times 10^7$ spores) to the pre-treated rice straw of the herbaceous biomass, and then culturing. The culture temperature is preferably 30° C. to 37° C., incubation time is preferably 40 to 72 hours.

It should be noted that the saccharifying enzyme produced by the transformant according to the present invention may be used in the saccharification reaction by bringing the transformant into direct contact with the base, or may be used as a saccharifying enzyme which is crudely or properly purified from the transformant.

EXAMPLES

Next, the present invention will be described in more detail based on a series of Examples, but the present invention is not limited to the following Examples.

Reference Example 1

The strains of *Aspergillus oryzae* and *Aspergillus awamori* (strain RIB40, strain RIB128, strain AOK20, strain AOK2P, strain AOK27L, strain AOK65, strain AOK139, strain AOK210, strain AOK241, strain AOK1597, strain AOK1505, strain AOK1506, strain AOK1508, strain AOK1509 and strain AOK1510) (all strains were obtained from Akita Konno Co., Ltd.) were compared by calculating the enzyme production yield based on the total amount of the enzyme secreted extracellularly. Here, the term "enzyme production yield" refers to the amount of enzyme produced per the carbon source introduced, and it was calculated by the following formula.

Formula: [enzyme production yield]=[total amount of enzyme secreted]/[amount of dextrin charged].

More specifically, first, rice straw was pulverized to a size so as to pass through a mesh having an opening of 3 mm, and ammonia water at a concentration of 25% by mass based on the dry mass was mixed such that the mass ratio was 1:1. By holding the mixture obtained for 120 hours at room temperature (about 20° C.) and then heating to a temperature of 60 to 80° C. under reduced pressure, ammonia is vaporized and separated to thereby produce ammonia-treated rice straw.

Separately, each *Aspergillus* strain was cultured for 1 week in a Czapek-Dox (CD) medium (containing 3% (wt/vol) dextrin, 0.1% (wt/vol) potassium dihydrogen phosphate, 0.2% (wt/vol) potassium chloride, 0.05% (wt/vol) magnesium sulfate, 0.001% (wt/vol) iron sulfate and 0.3% (wt/vol) sodium nitrate), thereby preparing a spore suspension.

1 mL of a 10% solution of dextrin (manufactured by Wako Pure Chemical Industries, Ltd.) was added to 1 g of the ammonia-treated rice straw (water content: about 10%), and 0.085 mL of 2M hydrochloric acid (manufactured by Wako Pure Chemical Industries, Ltd.) was further added thereto to adjust the pH to 6, thereby preparing a substrate sample as a base. For the pH measurement, 5 mL of ultrapure water was added to 1 g of the substrate sample, and the pH of the suspended solution was measured.

Next, 5 g of the substrate sample was weighed and placed in a 50 mL volume plastic tube (manufactured by Becton, Dickinson and Company), and was autoclaved at a condition of 121° C. for 15 minutes. The substrate sample following the autoclaving was inoculated with $1 \times 10^6$ spores, and, after stirring, transferred to a sterile petri dish (manufactured by Asahi Glass Co., Ltd.) and cultured for 40 hours at 30° C. and 95% RH. In addition, at the same time, a sample which was not inoculated with spores (negative control) was also treated in the same manner.

The total amount of the substrate after cultivation was collected into a 50 mL volume plastic tube, 15 mL of a 0.5% solution of sodium chloride (manufactured by Wako Pure Chemical Industries, Ltd.) was added thereto and stirred, and the resultant was allowed to stand for 2 hours at 4° C. Following standing, the resultant was centrifuged for 10 minutes at 10,000×g at 4° C., and the resulting supernatant was processed with a sterile filter (manufactured by Merck KGaA), thereby obtaining an enzyme solution.

SDS-PAGE was carried out using 10 µL of the thus obtained enzyme solution, and the total amount of secreted enzyme was calculated from the intensity of the resulting bands. The negative control was analyzed by HPLC to calculate the charged amount of dextrin. From the obtained total amount of secreted enzyme and the charged amount of dextrin, the enzyme production yield was calculated based on the aforementioned formula.

FIG. 1 shows the enzyme production yield by each strain. As a result, the AOK27L strain exhibited the highest enzyme production capacity among the *Aspergillus oryzae* strains used for screening, and exhibited a higher enzyme production capacity by about 2-fold compared to that of the *Aspergillus oryzae* strain RIB40, which was commonly used.

Example 1

Production of HO1 Strain

The pyrG gene was deleted from the AOK27L strain by genetic recombination through a protoplast-PEG method to obtain an *Aspergillus oryzae* strain HO1 exhibiting auxotrophy for uridine and high enzyme productivity in solid culture.

More specifically, first, by using the genomic DNA of the AOK27L strain (obtained from Akita Konno Co., Ltd.) as a template and amplifying the upstream sequence of the pyrG gene (SEQ ID NO: 3) with a primer 1 (SEQ ID NO: 1) and primer 2 (SEQ ID NO: 2) and the downstream sequence of the pyrG gene (SEQ ID NO: 6) with a primer 3 (SEQ ID NO: 4) and primer 4 (SEQ ID NO: 5) by PCR, respectively, followed by purification, gene fragments of the sequences upstream and downstream of the pyrG gene were obtained. A commercially available DNA polymerase (product name: KOD FX neo, manufactured by Toyobo Co., Ltd.) was used for the PCR, and a commercially available purification kit (product name: QIAquick PCR purification kit, manufactured by QIAGEN) was used for the purification.

Separately, the plasmid pRI910 (manufactured by Takara Bio Inc.) was treated with the restriction enzyme Sma I (manufactured by Takara Bio Inc.) at 30° C. and purified using the aforementioned purification kit to obtain a digested product of the plasmid (gene fragment).

The thus obtained three gene fragments were treated using the In-Fusion (registered trademark) HD Cloning Kit (manufactured by Takara Bio Inc.), and the resultant was used to transform *E. coli* strain HST08 (manufactured by Takara Bio Inc.) to obtain a plasmid pRI-AoΔpyrG.

The PCR amplification was carried out using the primers 1 and 4, a DNA polymerase (product name: KOD-plus-ver.2, manufactured by Toyobo Co., Ltd.) and the obtained plasmid pRI-AoΔpyrG as a template, and the resulting product was purified using the aforementioned purification kit to obtain a gene fragment (AoΔpyrG fragment) for the transformation of *Aspergillus* strains.

In accordance with the conventional procedure of PEG-calcium method, the AOK27L strain was transformed using the AoΔpyrG fragment. A plate medium was prepared by adding, to the CD culture medium, 5-fluoroorotic acid monohydrate (manufactured by Wako Pure Chemical Industries, Ltd.) to a final concentration of 1 mg/mL and uridine (manufactured by Sigma-Aldrich) to a final concentration of 20 mM, and then a strain which could grow on this plate medium was selected from the processed products of transformation to obtain the HO1 strain which was a pyrG gene-deficient strain.

It should be noted that the H01 strain is a newly produced strain and has excellent properties such that it is suitable for solid culture and an efficient genetic recombination is also possible. Therefore, the applicant of the present invention has international deposited the H01 strain to the Patent Microorganisms Depositary (NPDM) of the National Institute of Technology and Evaluation (NITE) (Room No. 122, 2-5-8 Kazusakamatari, Kisarazu, Chiba, Japan) as a novel microorganism (date of deposition: Nov. 12, 2013). The Accession number is NITE BP-01749. All restrictions imposed by the depositor on the availability to the public of the deposited biological material will be irrevocably removed upon granting of a patent on the present application.

(Production of HO2 Strain)

An *Aspergillus oryzae* strain HO2 (hereinafter, abbreviated as the "HO2 strain" in some cases) exhibiting auxotrophy for uridine and high enzyme productivity in solid culture was obtained by deleting the ligD gene from the HO1 strain using a marker recycling method.

More specifically, by using the genomic DNA of the HO1 strain as a template and amplifying the upstream sequence of the ligD gene (SEQ ID NO: 9) with a primer 5 (SEQ ID NO: 7) and primer 6 (SEQ ID NO: 8), the downstream sequence of the ligD gene (SEQ ID NO: 12) with a primer 7 (SEQ ID NO: 10) and primer 8 (SEQ ID NO: 11), the sequence for marker recycling (SEQ ID NO: 15) with a primer 9 (SEQ ID NO: 13) and primer 10 (SEQ ID NO: 14) and the pyrG gene (SEQ ID NO: 18) with a primer 11 (SEQ ID NO: 16) and primer 12 (SEQ ID NO: 17) by PCR, respectively, followed by purification, each of the gene fragments was obtained. A commercially available DNA polymerase (product name: KOD FX neo, manufactured by Toyobo Co., Ltd.) was used for the PCR, and a commercially available purification kit (product name: QIAquick PCR purification kit, manufactured by QIAGEN) was used for the purification.

Separately, the plasmid pRI910 (manufactured by Takara Bio Inc.) was treated with the restriction enzyme Sma I (manufactured by Takara Bio Inc.) at 30° C. and purified using the aforementioned purification kit to obtain a digested product of the plasmid (gene fragment).

Subsequently, the gene fragment of the upstream sequence of the ligD gene, the gene fragment of the downstream sequence of the ligD gene and the gene fragment of the plasmid pRI910 were treated using the In-Fusion (registered trademark) HD Cloning Kit (manufactured by Takara Bio Inc.), and the resultant was used to transform *E. coli* strain HST08 (manufactured by Takara Bio Inc.) to obtain a plasmid pRI-AoΔligD.

The resulting plasmid pRI-AoΔligD was treated with the restriction enzyme Sma I (manufactured by Takara Bio Inc.) at 30° C. and purified using the aforementioned purification kit to obtain a digested product of the plasmid (gene fragment).

The gene fragment of the resulting plasmid pRI-AoΔligD and the gene fragment of the pyrG gene were treated using the In-Fusion (registered trademark) HD Cloning Kit (manufactured by Takara Bio Inc.), and the resultant was used to transform *E. coli* strain HST08 (manufactured by Takara Bio Inc.) to obtain a plasmid pRI-AoΔligD::pyrG in which the pyrG gene was introduced between the upstream sequence and downstream sequence of the ligD gene.

Then, the plasmid pRI-AoΔligD::pyrG was treated with the restriction enzyme Sma I (manufactured by Takara Bio Inc.) at 30° C. and purified using the aforementioned purification kit to obtain a digested product of the plasmid (gene fragment).

The gene fragment of the resulting plasmid pRI-AoΔligD::pyrG and the gene fragment of the sequence for marker recycling pyrG gene were treated using the In-Fusion (registered trademark) HD Cloning Kit (manufactured by Takara Bio Inc.), and the resultant was used to transform *E. coli* strain HST08 (manufactured by Takara Bio Inc.) to obtain a plasmid pRI-AoΔligD::pyrGR in which the sequence for marker recycling was introduced between the pyrG gene and the downstream sequence of the ligD gene.

The PCR amplification was carried out using the primers 5 and 8, a DNA polymerase (product name: KOD-plus-ver.2, manufactured by Toyobo Co., Ltd.) and the obtained plasmid pRI-AoΔligD::pyrGR as a template, and the resulting product was purified using the aforementioned purification kit to obtain a gene fragment (AoΔligD::pyrGR fragment, corresponding to the "fragment for ligD deletion" in FIG. 1) for the transformation of *Aspergillus* strains.

In accordance with the conventional procedure of PEG-calcium method, the HO1 strain was transformed using the AoΔligD::pyrGR fragment. Then a strain which could grow on the CD plate medium was selected from the processed products of transformation to obtain a ligD gene-deficient strain.

Figure 3:
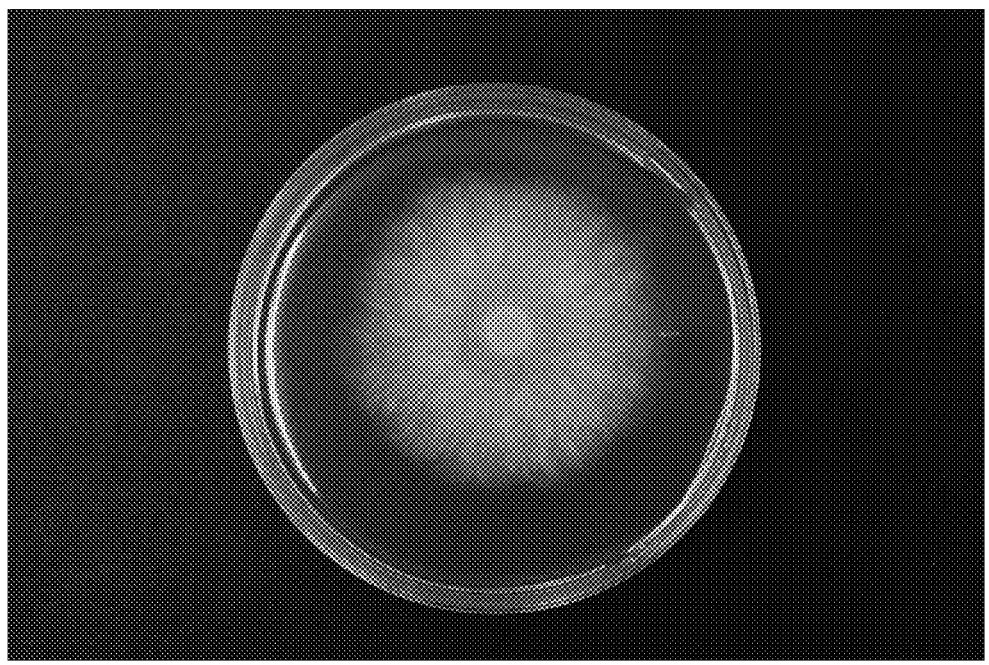
FIG. 3 is a photographic view of a uridine-containing CD plate medium following the incubation of the *Aspergillus oryzae* strain HO2 for 120 hours in Example 1.
Figure 4:
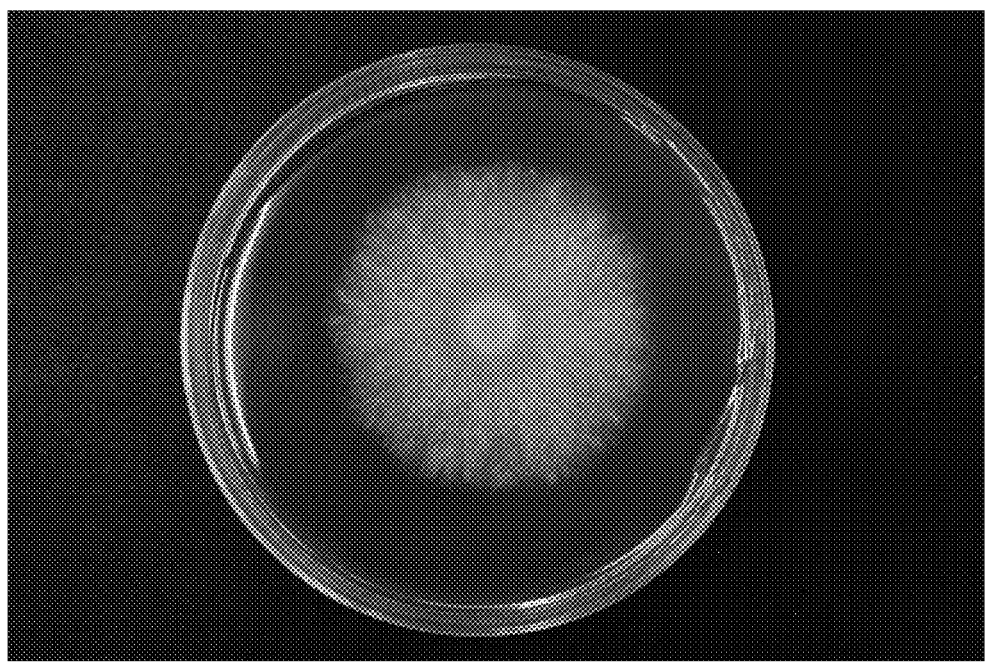
FIG. 4 is a photographic view of a uridine-containing CD plate medium following the incubation of the *Aspergillus oryzae* strain HO1 for 120 hours in Example 1.
Figure 5:
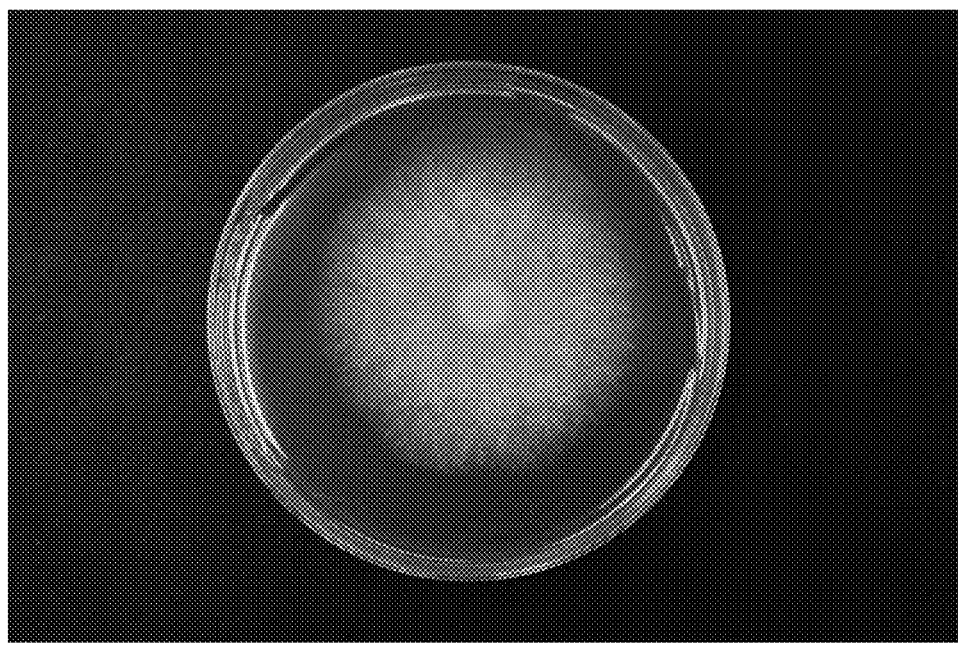
FIG. 5 is a photographic view of a uridine-containing CD plate medium following the incubation of the *Aspergillus oryzae* strain AOK27L for 120 hours in Example 1.

The spore suspension of the obtained ligD gene-deficient strain was inoculated, so as to achieve a concentration of $1 \times 10^6$ spores/plate, into a plate medium (uridine-containing CD plate medium) prepared by adding, to the CD culture medium, 5-fluoroorotic acid monohydrate to a final concentration of 1 mg/mL and uridine to a final concentration of 20 mM, and then a strain which could grow was selected, thereby obtaining the two gene-deficient HO2 strain which lacked both the ligD gene and the pyrG gene. FIGS. 3 to 5 show photographs of uridine-containing CD plate medium after 120 hours of incubation. When cultured on the uridine-containing CD plate medium, the HO2 strain (FIG. 3) grew equally well as the HO1 strain (FIG. 4) which was the parent strain and the AOK27L strain (FIG. 5).

It should be noted that the H02 strain is a newly produced strain and has excellent properties such that it is suitable for solid culture and an efficient genetic recombination at a targeted site within the chromosome is also possible. Therefore, the applicant of the present invention has international deposited the H02 strain to the Patent Microorganisms Depositary (NPDM) of the National Institute of Technology and Evaluation (NITE) (Room No. 122, 2-5-8 Kazusakamatari, Kisarazu, Chiba, Japan) as a novel microorganism (date of deposition: Nov. 12, 2013). The Accession number is NITE BP-01750. All restrictions imposed by the depositor on the availability to the public of the deposited biological material will be irrevocably removed upon granting of a patent on the present application.

While preferred embodiments of the invention have been described and illustrated above, it should be understood that these are exemplary of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

[Accession Number]
  NITE BP-01749
  NITE BP-01750
[Sequence Listing]

---

What is claimed is:

1. An *Aspergillus* mutant strain obtained by deleting a ligD gene from an auxotrophic mutant strain of *Aspergillus oryzae* strain AOK27L.

2. The *Aspergillus* mutant strain according to claim 1, wherein said auxotrophic mutant strain is a uridine auxotrophic mutant strain of *Aspergillus oryzae* strain AOK27L in which a pyrG gene is completely or partially deleted.

3. The *Aspergillus* mutant strain according to claim 2, wherein said uridine auxotrophic mutant strain is an *Aspergillus oryzae* strain H01 (accession number: NITE BP-01749).

4. The *Aspergillus* mutant strain according to claim 1 which is an *Aspergillus oryzae* strain H02 (accession number: NITE BP-01750).

5. A transformant obtained by introducing a pyrG gene and a saccharifying enzyme gene into the *Aspergillus* mutant strain described in claim 2.

6. The transformant according to claim 5, wherein said saccharifying enzyme gene is at least one gene selected from the group consisting of a cellobiohydrolase gene, a β-glucosidase gene, an endoxylanase gene, an arabinofuranosidase gene, a glucuronidase gene and an endoglucanase gene.

7. The transformant according to claim 5, wherein said saccharifying enzyme gene is at least one gene selected from the group consisting of a cellobiohydrolase gene from *Acremonium cellulolyticus*, a β-glucosidase gene from *Acremonium cellulolyticus*, an endoxylanase gene from a fungus belonging to the genus *Thermoascus*, an arabinofuranosidase gene from *Acremonium cellulolyticus* and a glucuronidase gene from *Acremonium cellulolyticus*.

8. The transformant according to claim 5, wherein the pyrG gene and said saccharifying enzyme gene are incorporated into a chromosome.

9. A method of producing a saccharifying enzyme, the method comprising culturing the transformant described in claim 5 on a solid medium comprising herbaceous biomass.

10. The method of producing a saccharifying enzyme according to claim 9, wherein said herbaceous biomass is rice straw or corn stover.

* * * * *

SEQUENCE LISTING

```
<160> NUMBER OF SEQ ID NOS: 18

<210> SEQ ID NO 1
<211> LENGTH: 41
<212> TYPE: DNA
<213> ORGANISM: Artificial Sequence
<220> FEATURE:
<223> OTHER INFORMATION: Description of Artificial Sequence:Primer 1

<400> SEQUENCE: 1
tcgagctcgg taccccaga ggtgacttta tccaagattc c                    41

<210> SEQ ID NO 2
<211> LENGTH: 34
<212> TYPE: DNA
<213> ORGANISM: Artificial Sequence
<220> FEATURE:
<223> OTHER INFORMATION: Description of Artificial Sequence:Primer 2

<400> SEQUENCE: 2
cccgggcaat tgccgcgaaa aattaaattg aatc                           34

<210> SEQ ID NO 3
<211> LENGTH: 917
<212> TYPE: DNA
<213> ORGANISM: Aspergillus oryzae AOK27L
<220> FEATURE:
<223> OTHER INFORMATION: Upstream sequence of pyrG gene

<400> SEQUENCE: 3
ccagaggtga ctttatccaa gattccttca cgacactgga agaactgctt gaagagctgc      60
ctgagtcaat cagcttcaat atcgagataa gtaggttata tgctgccact ggtggttctc     120
cacttgcggg agacaaagct aacaacgtcc caatgaagag taccccaggc ttcatgaagc     180
tatagaagca ggtgtagcac cagtggctat tgaaatcaac accttcatcg acaaagcgct     240
tgagagactc ttttcttacg gcaacaaaaa acggaccatt atcctatcct catttactcc     300
cgagatctgc attttattgg ccatcaaaca acagacgtac cctgtgatgt tcatcactaa     360
```

```
tgccggcaag cctccagtta cggatcgaga gatgagggct gccagcatac agtccgctgt      420
tcgatttgcc aagaggtgga atttatctgg ccttgtcttt gcatctgagg cgctggtaat      480
gtgccccagg cttgtcagat atgttcaacg atcaggattg atctgtggat cctatggatc      540
tcagaacaat ataccagaaa atgcgaaggt aagtgcttct atattgatcc ttagtgcttt      600
caaactgtga tgtagaagtt gctcggtagc tgattaaata ttctagaccc aagccgctgc      660
tggaattgac attattatgg ccgatagggt tgggcttatt gctatgtccc tgaaaggata      720
tcaaaagcag gcaaaaagcc aggcataatc cccgcgtgga cggtacccta aggataggcc      780
ctaatcttat ctcatgtgga ctgcatcgat gtgtttggtc aaaatgaggc atgtggctca      840
ccccacaggc ggagaaacgt gtggctagtg catgacagtc ccctccatag attcaattta      900 attttttcgcg gcaattg                                                     917

<210> SEQ ID NO 4
<211> LENGTH: 43
<212> TYPE: DNA
<213> ORGANISM: Artificial Sequence
<220> FEATURE:
<223> OTHER INFORMATION: Description of Artificial Sequence:Primer 3

<400> SEQUENCE: 4
cggcaattgc ccggggtagt ggtggatacg tactccttttt atg                        43

<210> SEQ ID NO 5
<211> LENGTH: 35
<212> TYPE: DNA
<213> ORGANISM: Artificial Sequence
<220> FEATURE:
<223> OTHER INFORMATION: Description of Artificial Sequence:Primer 4

<400> SEQUENCE: 5
ctctagagga tccccgttgc ggatcttgct gcttg                                  35

<210> SEQ ID NO 6
<211> LENGTH: 1000
<212> TYPE: DNA
<213> ORGANISM: Aspergillus oryzae AOK27L
<220> FEATURE:
<223> OTHER INFORMATION: Downstream sequence of pyrG gene

<400> SEQUENCE: 6
gtagtggtgg atacgtactc cttttatggc agtatgtcgc aagtatgatg cgatttataa       60
attcagcact cgaaatgact actactatgt gtctacgaca gataccctct ccgtacgaat      120
aagacacctg cctcgatata tggacaaatt caaaatcagg gtcaagggtc atgtttcaaa      180
gtcacaacaa tctccaacat agacgagaat ttgtaccgga gtgtctgaag gtgcagctgg      240
agattggtct atttttcttag agtggggtat cactaatgta cagtcggtca ctatcgtaca      300
aacaatcaca attatataca agatttccca ccacccccta ctctaacacg gcacaattat      360
ccatcgagtc agagcctagc caccatttgg tgctctcgta gagaccaaag tataatcctg      420
atccgacagc ggccataaac gtgttgatag cacaccctcg gaatagtcct ctcgggccat      480
ctgttcgtac aatctcccgt acggtattga tcatcctttt cttctgaggt gcagttgtat      540
ctgcagcatc gagcatgatt cgtgtccgga ccatatccat gggtgctgtc aagacactag      600
ctataccgcc cgagaccgca gcacttattg cggctgtcgc tgcagcctct ccgattgtcg      660
aatgggcctc tttctttcca tactctcttg gtctttctag caccttctct cgatctccga      720
```

```
atctatattc aaaaattcga taccgaaaag actcgtacag aggcatctga atcgccgaca      780
ctggcaagct atgcgccaca agagccgggt atccgctcca aagctgtcta gggttgataa      840
acttcttgaa agctagccgt gtcgctttct gggctacacc acctaccctt cccccagcta      900
caggtgctga tgcgtctgga tggtgtgatt ggatcatctg cgcgttgtgt tttaatgcat      960
cagccggagc aaagactccg caagcagcaa gatccgcaac                           1000

<210> SEQ ID NO 7
<211> LENGTH: 39
<212> TYPE: DNA
<213> ORGANISM: Artificial Sequence
<220> FEATURE:
<223> OTHER INFORMATION: Description of Artificial Sequence:Primer 5

<400> SEQUENCE: 7
tcgagctcgg tacccggtta ctgctctccc ttgatgatg                             39

<210> SEQ ID NO 8
<211> LENGTH: 27
<212> TYPE: DNA
<213> ORGANISM: Artificial Sequence
<220> FEATURE:
<223> OTHER INFORMATION: Description of Artificial Sequence:Primer 6

<400> SEQUENCE: 8
taggtagtga acctatttcg agagcag                                          27

<210> SEQ ID NO 9
<211> LENGTH: 1455
<212> TYPE: DNA
<213> ORGANISM: Aspergillus oryzae AOK27L
<220> FEATURE:
<223> OTHER INFORMATION: Upstream sequence of ligD gene

<400> SEQUENCE: 9
gcaacttgag cgagcacata gttgacaaag ataatagctt ttggactgta tgcttgcgta      60
ccacttcgaa agtcggttac tgctctccct tgatgatggt caagctccac taccatcagg     120
cgagagcctc tggcgagcaa gctccgctga tgcctgggca agactttacg aaaagactac     180
aggtatttct cctgtccctt tttcatgcgt aattctgtct aacctgcgcc ccttaggtcg     240
agaggaggtt tctctctata acgctgtgct tacgctgtat attgagaaga agcttgttgc     300
taatatagga gaattcggtc acatcttatt aatccacgca ctttaccatc gaatgtggga     360
ggtgggtgac tatttccgcc gtcctttgtc tttctggaat cctactgcca agaagcagcc     420
tagggaagct gcgattccct cgggatctgt ttggctaccg ggtataccct catattcgag     480
gtggcgtaat agcgcgtgtg attgcctgga tattctccat tgggcagcaa atagcacgat     540
agccaaggca tctggcctcg agcacccgac cgtcctacac cttcacgaag cccggattat     600
attgctcgta ccctttcatg agattaagac cttggtaaca tctctagcaa cagaaaaagt     660
tcaatggagc gcacgtcagc agacgattga gtggcattat atacttcgtt ggattaaaca     720
cgatcaatat aaggcccggc tcgcggttat acacgcaggc gcatctttgt ggcatgtgcg     780
aagatattcg accgatgcat ttcatgagcc ggtagctgtg tttcttgcaa tacttacttt     840
atgggcctat ggcatgtgtc attcgcaggt gtttccagat attaaatccc gtggtggccc     900
agatgagaat ttgcccagcg agccacgtt cttccatatc gaccgtcctt gtgacgacga      960
gctcgtacag atctttgttc gaggagggca agggatgaag ggtaatgtga ctggtgtggg    1020
ggatatatgt gctccagaag gtcctgaacg gattctccag gttggctgcg agacgcttgc    1080
```

```
tggccttact tcttggggaa tatctaagag atttattgca atcctgacaa ggctcgggga      1140
cttgatgtca tgcgacaaat aaatagcctt ggtgtacagc tacaatttct tacatttcct      1200
ctctctctct tgttggcaa accattcttt ctttggttac tcaataccct atcatagctt       1260
agtttatgtg aaagagaatt agattctgac aaccgtgacg ataaatggga atatctactt      1320
gtctaaaggc ggtgatgagc ataagttcgt atgacgtcac atggttccgg gtgaagtcaa      1380
tttatcttat cgttgcctat tgcagcctag acctcaacag aagatataaa ctagtattcc      1440
atgcactctg ctctc                                                       1455

<210> SEQ ID NO 10
<211> LENGTH: 45
<212> TYPE: DNA
<213> ORGANISM: Artificial Sequence
<220> FEATURE:
<223> OTHER INFORMATION: Description of Artificial Sequence:Primer 7

<400> SEQUENCE: 10
taggttcact acctagcggc cgcacaggca ccttgcatca tcatc                      45

<210> SEQ ID NO 11
<211> LENGTH: 37
<212> TYPE: DNA
<213> ORGANISM: Artificial Sequence
<220> FEATURE:
<223> OTHER INFORMATION: Description of Artificial Sequence:Primer 8

<400> SEQUENCE: 11
ctctagagga tccccggacc gacgattcgt tgaagag                               37

<210> SEQ ID NO 12
<211> LENGTH: 1346
<212> TYPE: DNA
<213> ORGANISM: Aspergillus oryzae AOK27L
<220> FEATURE:
<223> OTHER INFORMATION: Downstream sequence of ligD gene

<400> SEQUENCE: 12
gggcatttcc catgggccta acccaaatcc aaattcatac accggtgctg ccgacgatgc      60
acaagatact ttcccaattg tacatacatc catacatacc cccattttg cgtaatgaca      120 catccacttt ggatgaaccg aaaaagacca cataaaacta tcctacttgc ccagttcctt      180
ggttatctgc aaccctgccc aaacacggaa catggcggga gtttgctcca aaacacggcg      240
taaagttaag cccgaccaga gaatccatct tctaccattg gacagagata aggcctacag      300
gggagaacga gacatggcca tgcaaacagg ggagaaataa gatccatcca tggatagaga      360
tgacctagct gatgcattac agcctgaatg aataccatac agtaatataa tcccttgaac      420
tgaaagataa gaagaccact ctggattggg tttagcttat gtcgaagttt tagataaccc      480
taatacaaac cagacttatc ccaacactac gcaaagatc ctcccatctc tcgaaagaac      540
gagacggtcg agaatctgta tttactatca tctttccatg ataagtggta gttaagagtc      600
tcatcgtgct atgaattata gcggtcacct cattcctgat ctagttcttc cttaatcatt      660
tgactcgaat agtttctagt ttgattagag gatagtgttc tttttagaat agatacgaca      720
cacgtcttca ttctcacttc atctttcgat agattcatta gattgcatct aggcttggat      780
gcaacataaa ctctgcgact ttgctcggcc ttgtctctat cacattatgt cctactcctt      840
tcctaaaggt aaaaaaaaat atgtatggca gctcgatagt catttagcta ccccatatcc      900
```

```
gagagtatat ccgaaaaaca atgtagacca agagtgaaag ttgaacaaga gggacccatc    960
gacattttgt cctgtctagg gacggagatt aagactgttt tcgagtcagt ctcgcattct   1020
tttcccggcc ttactctata catagaaagg aattcttccc acattagcct cgtatacttt   1080
taaggagtcc gcagctgaag atgggacaca agctgacggc cattacgact ataggtatag   1140
agtacgaggg tgttggatta aatcatcagt tggcctggaa atgtcggcga atggatatgt   1200
gtgtcgatga atagacagca gctctcaagt atggagaaag gcttacaata atactgtggt   1260
tatggtcttc gaatgctacc tttgagtgtc acagctcaga aaagggcatc gctaaggcac   1320
cgtctatctc ttcaacgaat cgtcgg                                        1346

<210> SEQ ID NO 13
<211> LENGTH: 37
<212> TYPE: DNA
<213> ORGANISM: Artificial Sequence
<220> FEATURE:
<223> OTHER INFORMATION: Description of Artificial Sequence:Primer 9

<400> SEQUENCE: 13
aggtatcgaa ttcccgacga gctcgtacag atctttg                              37

<210> SEQ ID NO 14
<211> LENGTH: 42
<212> TYPE: DNA
<213> ORGANISM: Artificial Sequence
<220> FEATURE:
<223> OTHER INFORMATION: Description of Artificial Sequence:Primer 10

<400> SEQUENCE: 14
ccatgggaaa tgcccgggag agcagagtgc atggaatact ag                        42

<210> SEQ ID NO 15
<211> LENGTH: 500
<212> TYPE: DNA
<213> ORGANISM: Aspergillus oryzae AOK27L
<220> FEATURE:
<223> OTHER INFORMATION: Sequence for marker recycling

<400> SEQUENCE: 15
gacgagctcg tacagatctt tgttcgagga gggcaaggga tgaagggtaa tgtgactggt     60 gtggggata tatgtgctcc agaaggtcct gaacggattc tccaggttgg ctgcgagacg    120
cttgctggcc ttacttcttg gggaatatct aagagattta ttgcaatcct gacaaggctc    180
ggggacttga tgtcatgcga caaataaata gccttggtgt acagctacaa tttcttacat    240
ttcctctctc tctctttgtt ggcaaaccat tctttctttg gttactcaat accctatcat    300
agcttagttt atgtgaaaga gaattagatt ctgacaaccg tgacgataaa tgggaatatc    360
tacttgtcta aaggcggtga tgagcataag ttcgtatgac gtcacatggt tccgggtgaa    420
gtcaatttat cttatcgttg cctattgcag cctagacctc aacagaagat ataaactagt    480
attccatgca ctctgctctc                                               500

<210> SEQ ID NO 16
<211> LENGTH: 48
<212> TYPE: DNA
<213> ORGANISM: Artificial Sequence
<220> FEATURE:
<223> OTHER INFORMATION: Description of Artificial Sequence:Primer 11

<400> SEQUENCE: 16
gcactctgct ctcccggtgg tgggaaatct tgtatataat tgtgattg                  48
```

<210> SEQ ID NO 17
<211> LENGTH: 44
<212> TYPE: DNA
<213> ORGANISM: Artificial Sequence
<220> FEATURE:
<223> OTHER INFORMATION: Description of Artificial Sequence:Primer 12

<400> SEQUENCE: 17
ccatgggaaa tgcccgggcg acactggaag aactgcttga agag    44

<210> SEQ ID NO 18
<211> LENGTH: 2300
<212> TYPE: DNA
<213> ORGANISM: Aspergillus oryzae AOK27L
<220> FEATURE:
<223> OTHER INFORMATION: pyrG gene

<400> SEQUENCE: 18

| | |
|---|---|
| cgacactgga agaactgctt gaagagctgc ctgagtcaat cagcttcaat atcgagataa | 60 |
| gtaggttata tgctgccact ggtggttctc cacttgcggg agacaaagct aacaacgtcc | 120 |
| caatgaagag tacccaggc ttcatgaagc tatagaagca ggtgtagcac cagtggctat | 180 |
| tgaaatcaac accttcatcg acaaagcgct tgagagactc ttttcttacg gcaacaaaaa | 240 |
| acggaccatt atcctatcct catttactcc cgagatctgc attttattgg ccatcaaaca | 300 |
| acagacgtac cctgtgatgt tcatcactaa tgccggcaag cctccagtta cggatcgaga | 360 |
| gatgagggct gccagcatac agtccgctgt tcgatttgcc aagaggtgga atttatctgg | 420 |
| ccttgtcttt gcatctgagg cgctggtaat gtgcccagg cttgtcagat atgttcaacg | 480 |
| atcaggattg atctgtggat cctatggatc tcagaacaat ataccagaaa atgcgaaggt | 540 |
| aagtgcttct atattgatcc ttagtgcttt caaactgtga tgtagaagtt gctcggtagc | 600 |
| tgattaaaata ttctagaccc aagccgctgc tggaattgac attattatgg ccgatagggt | 660 |
| tgggcttatt gctatgtccc tgaaaggata tcaaaagcag gcaaaaagcc aggcataatc | 720 |
| cccgcgtgga cggtaccta aggataggcc ctaatcttat ctacatgtga ctgcatcgat | 780 |
| gtgtttggtc aaaatgaggc atgtggctca ccccacaggc ggagaaacgt gtggctagtg | 840 |
| catgacagtc ccctccatag attcaattta atttttcgcg gcaattgtcg tgcagtttgt | 900 |
| atctacattt cattccatat atcaagagtt agtagttgga catcctgatt atttttgtcta | 960 |
| attactgaaa actcgaagta ctaacctact aataagccag tttcaaccac taagtgctca | 1020 |
| tttatacaat atttgcagaa ccccgcgcta cccctccatc gccaacatgt cttccaagtc | 1080 |
| gcaattgacc tacagcgcac gcgctagcaa gcaccccaat gcgctcgtaa agaagctctt | 1140 |
| cgaggttgcc gaggccaaga aaaccaatgt caccgtttcc gccgacgtga caaccaccaa | 1200 |
| agagctgctg gatttggctg accgtatgcg caccggggat gccacttaca tgtgatctag | 1260 |
| taatggttaa tggtggatta taacagga ctcggtccgt acattgccgt gatcaaaact | 1320 |
| cacatcgata tcctctccga tttcagcgaa gaaaccatca ccggtctgaa ggcccttgca | 1380 |
| gagaagcaca atttcctcat cttcgaagat cgcaagttca tcgatatcgg aaacacagtc | 1440 |
| caaaagcagt accatggcgg cactctgcgt atctctgagt gggcccacat catcaactgc | 1500 |
| agtattctgc ccggtgaggg tatcgtcgag gctctggccc agactgcttc ggccgaggac | 1560 |
| ttcccctacg gctccgagag gggccttttg atccttgcgg agatgacctc caagggatct | 1620 |
| ttggctaccg gtcaatatac tacttcttct gttgactatg ctcggaagta taagaagttt | 1680 |

```
gtgatgggat tcgtctcgac acgtcacctt ggcgaggttc agtctgaagt tagctcgcct    1740
tcggaggagg aagattttgt cgtcttcacg acaggtgtca acctctcctc gaagggtgac    1800
aagctgggac agcagtacca aactcctgag tcggctgttg gacgcggtgc cgactttatt    1860
attgctggcc gtggaattta tgctgctcct gatcccgtgg aggcggcgaa gcagtaccag    1920
aaggagggat gggatgcata cctgaagcgt gttggtgcgc aataagtagt ggtggatacg    1980
tactcctttt atggcagtat gtcgcaagta tgatgcgatt tataaattca gcactcgaaa    2040
tgactactac tatgtgtcta cgacagatac cctctccgta cgaataagac acctgcctcg    2100
atatatggac aaattcaaaa tcagggtcaa gggtcatgtt tcaaagtcac aacaatctcc    2160
aacatagacg agaatttgta ccggagtgtc tgaaggtgca gctggagatt ggtctatttt    2220
cttagagtgg ggtatcacta atgtacagtc ggtcactatc gtacaaacaa tcacaattat    2280
atacaagatt tcccaccacc                                                2300
```